United States Patent [19]

Kim et al.

[11] Patent Number: 4,957,915
[45] Date of Patent: Sep. 18, 1990

[54] BENZODIAZEPINE ANALOGS

[75] Inventors: Sun H. Kim, Chestnut Hill; John E. Taylor, Upton, both of Mass.

[73] Assignee: Biomeasure, Inc., Hopkinton, Mass.

[21] Appl. No.: 316,463

[22] Filed: Feb. 27, 1989

[51] Int. Cl.$^5$ .................... C07D 243/14; A61K 31/55
[52] U.S. Cl. ..................................... 514/221; 540/509
[58] Field of Search ......................... 540/509; 314/221

[56] References Cited

U.S. PATENT DOCUMENTS

| | | | |
|---|---|---|---|
| 4,631,285 | 12/1986 | Petersen et al. | 514/292 |
| 4,647,560 | 3/1987 | Boltz et al. | 514/220 |
| 4,738,973 | 4/1988 | Gittos | 514/328 |

FOREIGN PATENT DOCUMENTS

| | | | |
|---|---|---|---|
| 0270494 | 11/1986 | European Pat. Off. | 546/119 |
| 1034872 | 7/1966 | United Kingdom | 540/509 |

OTHER PUBLICATIONS

Kulkarni et al., "Synthesis of 3-Substituted-amino/aroyloxy-7-chloro-5-phenyl 1,3 dihydro-2H-1,4-benzodiazepine-2-ones as Possible Anxiolytics" *J. Indian Chem. Soc.*, vol. LXIII, pp. 425-426.

(List continued on next page.)

Primary Examiner—Robert T. Bond
Attorney, Agent, or Firm—Fish & Richardson

[57] ABSTRACT

BZDs of the general formula 1:

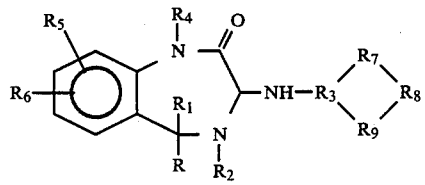

(1)

where: R represents H, alkyl, alkenyl, cycloalkyl or cycloalkenyl each with up to 8 carbon atoms, phenylalkyl with an alkylene chain of 1 to 3 carbon atoms and optionally substituted on the phenyl radical with one or two substituents selected from the group consisting of Cl, Br, F, CN, $CF_3$, $NO_2$, lower alkyl, and $OCH_3$, or represents a phenyl radical which is optionally substituted with one or two substituents selected from the group consisting of Cl, F, Br, CN, I, $CF_3$ $NO_2$, lower alkyl and $OCH_3$, or represents a 5-membered or 6-membered heterocyclic radical with 1 or 2 heteroatoms from the group consisting of O, N and S; $R_1$ represents H or, together with $R_2$, forms a bond; $R_2$ and $R_4$ independently of one another represent H, or an alkyl radical with 1 to 6 carbon atoms, or represent a phenylalkyl radical with an alkyl chain of 1 to 3 carbon atoms and optionally substituted on the phenyl radical with one or two substituents selected from the group consisting of Cl, Br, F, CN, $CF_3$, $NO_2$, $CH_3$, $C_2H_5$ and $OCH_3$, or $R_2$ together with $R_1$, forms a bond; $R_3$ is $(CH_2)_n CH$ or $(CH_2)_n$—$CR_{14}$ =$CR_{14}$, where n is between 0 and 5 inclusive and $R_{14}$=HOL a bond; $R_5$ and $R_6$ independently of one another represent H, Cl, F, Br, $NO_2$, CN, $CF_3$, lower alkyl, or $OCH_3$; $R_7$ and $R_9$ are independently $CH_2$ or C=O; $R_8$ is

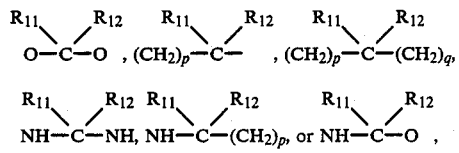

where p and q are independently between 0 and 4 and the sum of p and q is 4 or less; and $R_{11}$ and $R_{12}$ are independently H or a lower alkyl of between 1 and 5 carbon atoms.

13 Claims, 1 Drawing Sheet

OTHER PUBLICATIONS

Colotta et al., "Synthesis, Binding Studies, and Structure-Activity Relationships of 1-Aryl- and 2-Aryl[1-]benzopyranopyrazol-4-ones, Central Benzodiazepine Receptor Ligands", *J. Medicinal Chem.*, vol. 31, No. 1, Jan. 1988.

Yokoyama et al., "2-Arylpyrazolo[4,3-c]quinolin-3--ones: Novel Agonist, Partial Agonist, and Antagonist of Benzodiazepines", *J. Medicinal Chem.*, vol. 25, No. 4, pp. 337-339, 1982.

Trudell et al., "Synthesis of 7,12-Dihydropyrido[3,4-b:5,4-b']diindoles, A Novel Class of Rigid, Planar Benzodiazepine Receptor Ligands," *J. Medicinal Chem.*, vol. 30, No. 3, pp. 456-458, 1987.

Takada et al., "A New Thienylpyrazoloquinoline: A Potent and Orally Active Inverse Agonist to Benzodiazepine Receptors," *J. Medicinal Chem.*, vol. 30, No. 3, pp. 454-455, 1987.

Lister, "The Benzodiazepine Receptor Inverse Agonists FG 7142 and RO 15-4513 Both Reverse Some of the Behavioral Effects of Ethanol in Holeboard Test," *Life Sciences*, vol. 41, No. 12, pp. 1481-1489, 1987.

Braestrup et al., "Urinary and brain $\beta$-carboline-3-carboxylates as potent inhibitors of brain benzodiazepine receptors," *Proc. Nat. Acad. Sci. U.S.A.*, vol. 77, No. 4, pp. 2288-2292, Apr. 1980.

Mohler et al., "Photoaffinity Labeling of Benzodiazepine Receptors with a Partial Inverse Agonist," *European Journal of Pharmacology*, vol. 102, pp. 191-192, 1984.

Polc et al., "A Three-State Model of the Benzodiazepine Receptor Explains the Interactions Between the Benzodiazepine Antagonist Ro 15-1788, Benzodiazepine Tranquilizers, $\beta$-Carbolines, and Phenobarbitone," *Naunyn-Schmiedeberg's Arch. Pharmacol.*, vol. 321, No. 4, pp. 260-264, 1982.

Trullas et al., "3-Ethoxy-$\beta$-Carboline: A High Affinity Bezodiazepine Receptor Ligand with Partial Inverse Agonist Properties," *Life Sciences*, vol. 43, No. 15, pp. 1189-1197, 1988.

Sarter et al., "Treatment strategies for senile dementia: antagonist $\beta$-carbolies," *TINS*, vol. 11, No. 1, pp. 13-17, 1988.

Lavie, "RO 15-1788 Decreases Hypnotic Effects of Sleep Deprivation," *Life Sciences*, vol. 41, No. 2, pp. 227-233, 1987.

Venault et al., "Benzodiazepine impairs and $\beta$-carboiine enhances performance in learning and memory tasks," *Nature*, Vo. 321, pp. 864-866, Jun. 26, 1986.

Lal et al., "Enhancement of learning and memory in mice by a benzodiazepine antagonist," *The FASEB Journal*, vol. 2, No. 11, pp. 2707-2711, Aug. 1988.

Kemp et al., "The affinities, potencies and efficacies of some benzodiazepine-receptor agonists, antagonists and inverse-agonists at rat hippocampal $GABA_A$-receptors," *Br. J. Pharmac.*, vol. 91, No. 3, pp. 601-608, Jul. 1987.

Nutt, "Benzodiazepine dependence in the clinic: reason for anxiety," *TIPS*, vol. 7, pp. 457-460, Nov. 1986.

Squires and Braestrup, "Benzodiazepine receptors in rat brain," *Nature*, vol. 266, pp. 732-734, Apr. 21, 1977.

Lader, "Benzodiazepines—The Opium of the Masses?", *Neuroscience*, vol. 3, No. 2, pp. 159-165, Feb. 1978.

Hunkeler et al., "Selective antagonists of benzodiazepines,"*Nature*, vol. 290, pp. 514-516, Apr. 9, 1981.

Freidinger et al., "Design of Novel Antagonists of Cholecystokynin," *Topics in Medicinal Chemistry, 4th SCI-RSC Medicinal Chemistry Symposium*, Ed. by P. R. Leeming, Royal Society of Chemistry, 1988.

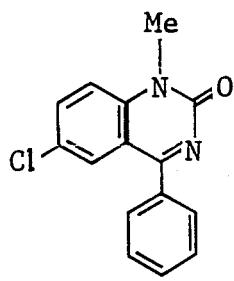
diazepam
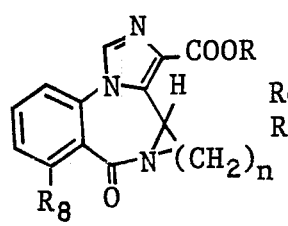
|  | R | $R_8$ | n |
|---|---|---|---|
| Ro16-6028 | $Bu^t$ | Br | 2 |
| Ro17-1812 | $CH_2$ | Cl | 3 |
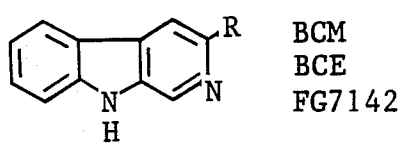
|  | R |
|---|---|
| BCM | COOMe |
| BCE | COOEt |
| FG7142 | CONHMe |
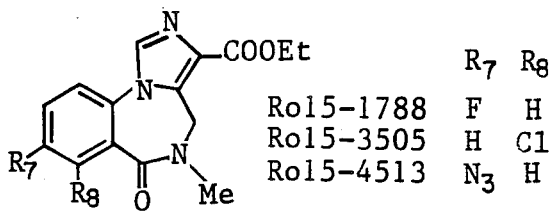
|  | $R_7$ | $R_8$ |
|---|---|---|
| Ro15-1788 | F | H |
| Ro15-3505 | H | Cl |
| Ro15-4513 | $N_3$ | H |
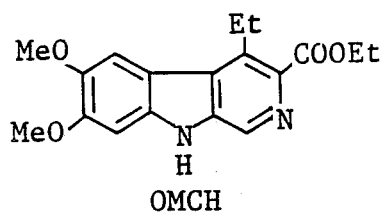
OMCH
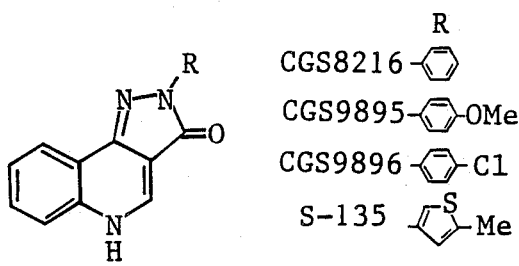
|  | R |
|---|---|
| CGS8216 | -Ph |
| CGS9895 | -Ph-OMe |
| CGS9896 | -Ph-Cl |
| S-135 | -thienyl-Me |
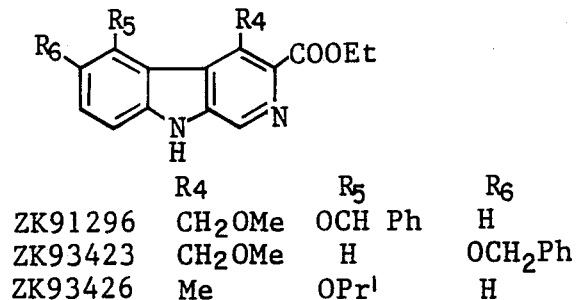
|  | $R_4$ | $R_5$ | $R_6$ |
|---|---|---|---|
| ZK91296 | $CH_2OMe$ | $OCH_2Ph$ | H |
| ZK93423 | $CH_2OMe$ | H | $OCH_2Ph$ |
| ZK93426 | Me | $OPr^i$ | H |
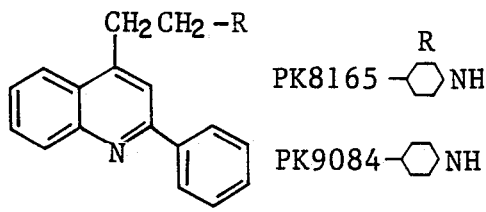
|  | R |
|---|---|
| PK8165 | -cyclohexyl-NH |
| PK9084 | -cyclohexyl-NH |
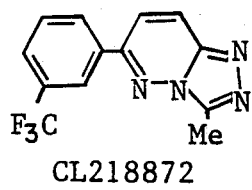
CL218872
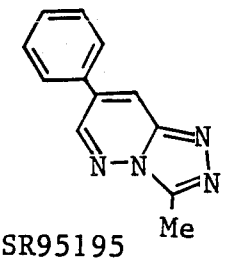
SR95195
FIGURE

BENZODIAZEPINE ANALOGS

BACKGROUND OF THE INVENTION

This invention relates to benzodiazepines having inverse agonist or antagonist properties, and to their therapeutic use.

Benzodiazepines (BZDs) are important therapeutic agents which act on the central nervous system as anxiolytic, hypnotic, and anti convulsant agents (Colotta et al., 31 J. Med. Chem. 1, 1988). They are also used as sedatives and muscle relaxants. One example is diazepam, the structure of which is shown in the FIGURE. The physiological effect of BZDs is dose dependent. For example, at low doses diazepam is anxiolytic and anti convulsant, and at higher doses it acts as a sedative and muscle relaxant.

BZDs interact with neuronal membrane proteins, termed BZD receptors, which may be located in GABA-ergic synapses and are classified as peripheral, neuronal, and central receptors. Referring to the FIGURE, examples of some compounds with affinity for these BZD receptors are shown. These compounds have diverse structures and give rise to different physiological effects. For example, the β-carbolines, ZK91296, ZK93426 and FG7142 are a partial agonist, antagonist, and partial inverse-agonist, respectively.

As used herein, an agonist refers to a compound having a similar physiological activity to a BZD, which produces a maximal response in a tissue even when it occupies less than all of the BZD receptor sites. A partial agonist is a compound having low efficacy, and producing a physiological response less than the tissue maximum, even when it occupies all available BZD receptor sites. Other examples of partial agonists include CL218872 and CGS9896 (the FIGURE) An inverse-agonist is a compound which produces the opposite physiological effect of an agonist; a partial inverse-agonist has some of the properties of an inverse-agonist. Examples of inverse-agonists include β-carboline derivatives such as 8CM, βCE and Ro 15-4513 (the FIGURE); examples of partial inverse agonists are 3-ethoxy-β-carboline and ZK90886. An antagonist is a compound which reduces or eliminates the physiological activity of an agonist or inverse-agonist on a tissue, and which has little intrinsic activity on the tissue by itself. Another example of an antagonist is Ro 15-1788 (the FIGURE). Partial agonists may also have some antagonist-like properties.

Dua et al. (63 J. Indian. Chem. Soc. 425, 1986) demonstrated that introduction of hydroxy, alkoxy, and carboxy groups at the 3-position of 1, 4 benzodiazepines produces anxiolytic compounds, i.e., BZD agonists. Introduction of a morpholino group or methoxy benzoyloxy group at this position also produces compounds with appreciable anxiolytic activity, but devoid of CNS depression activity, indicative of their BZD antagonistic nature. Id.

Boltze et al. U.S. Pat. No. 4,647,560, hereby incorporated by reference, describes BZDs, derived from 1,4 benzodiazepines, useful for treatment of cerebral disorders caused by old age, as well as disorders of learning and memory. These compounds have substitutions at the 3-position. including unsaturated ring structures. These compounds have no affinity for BZD receptors and show no anxiolytic activity, but exhibit potent phychotropic activity in animals.

SUMMARY OF THE INVENTION

The invention provides BZDs of the general formula

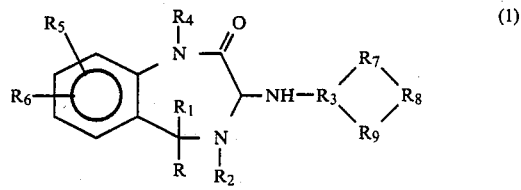

where:

R represents H, alkyl, alkenyl, cycloalkyl, or cycloalkenyl, each with up to 8 carbon atoms; phenylalkyl with an alkylene chain of 1 to 3 carbon atoms and optionally substituted on the phenyl radical with one or two substituents each independently selected from the group consisting of Cl, Br, F, CN, $CF_3$, $NO_2$, lower (Cl-5) alkyl, and $OCH_3$, or represents a phenyl radical which is optionally substituted with one or two substituents each independently selected from the group consisting of Cl, F, Br, CN, I, $CF_3$ $NO_2$, lower (Cl-5) alkyl, and $OCH_3$, or represents a 5-membered or 6-membered heterocyclic radical with 1 or 2 heteroatoms each independently selected from the group consisting of O, N and S; $R_1$ represents H or, together with $R_2$, forms a bond; $R_2$ and $R_4$ each independently represents H, or an alkyl radical with 1 to 6 carbon atoms, or represent a phenylalkyl radical with an alkyl chain of 1 to 3 carbon atoms and optionally substituted on the phenyl radical with one or two substituents each independently selected from the group consisting of Cl, Br, F, CN, $CF_3$, $NO_2$, lower (Cl-5) alkyl, and $OCH_3$, or $R_2$ together with $R_1$ forms a bond; $R_3$ is $(CH_2)_n CH$ or $(CH_2)_n-CR_{14}=CR_{14}$, where n is between 0 and 5 inclusive and $R_{14}=H_{06}$ or $R_5$ and $R_6$ each independently represents H, Cl, Br, F, CN, $CF_3$. $NO_2$, lower (Cl-5) alkyl, or $OCH_3$; $R_7$ and $R_9$ each independently represents $CH_2$ or $C=O$; $R_8$ is

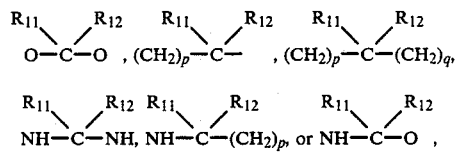

where p and q are independently between 0 and 4 and the sum of p and q is 4 or less; and $R_{11}$ and $R_{12}$ are independently H or a lower (Cl- 5) alkyl (Cl-5 means between 1 and 5 carbon atoms, inclusive.)

In preferred embodiments, R is

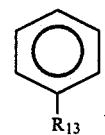

where $R_{13}$ is H or a halogen; $R_1$ is H; $R_2$ is H; $R_4$ is H or lower (Cl-5) alkyl; and $R_5$ and $R_6$ are, independently, H or a halogen; $R_3$ is $CH=C$; at least one of $R_7$ or $R_9$ is $C=O$; $R_8$ is

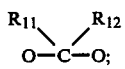

and $R_{11}$ and $R_{12}$ are both H.

Particular preferred compounds of the invention include 3(RS)-1,3-dihydro 3(2,2-dimethyl-4,6-dioxo-1,3-dioxan-5-ylidenemethyl)amino-1-methyl-5-phenyl-2H,1,4-benzodize pin-2-one; 3(RS)-1,3-dihydro-3-(2,2 dimethyl-4,6-dioxo-1,3 dioxan-5 ylidenemethyl)amino-7-chloro-1-methyl-5-phenyl-2H,1,4-benzodiazepin 2-one; and 3(RS)-1,3-dihydro3-(2,2-dimethyl 4,6-dioxo-1,3-dioxan-5-ylidenemethyl)amino-7-fluoro-1-methyl-5-phenyl-2H, 1,4-benzodiazepin-2-one. Where the compounds can occur in the form of optical antipodes, the invention features the racemate and the individual enantiomers. The racemate can be split by the customary route by salt formation with an optically active acid and fractional crystallization of the diastereomeric salts, or by chromatography on an optically active carrier material.

The BZDs of the present invention differ from prior BZDs in their structure and pharmacological action. The compounds according to the invention have no significant affinity for the peripheral BZD receptor, but have potent binding affinity for the neuronal BZD receptor. The BZDs potentiate pentylenetetrazole (PTZ)-induced convulsion, indicating their reverse agonist character at the central BZD receptor. Furthermore, they antagonise pentobarbital sleeping time in rats, indicating that they possess antagonist or stimulant activity. The BZDs of the invention facilitate learning and/or memory processes by reversing a negative modulatory influence of endogeneous diazepam-like ligands for BZD receptors. Thus, the BZDs are suitable for treatment of disorders in cerebral function caused by old age, such as the various forms of presenile and senile dementia o the Alzheimer type. They are also useful for treatment of alcohol and BZD dependence.

Compositions for treating cerebral disorders include an amount effective therefore of a compound of the invention, in an admixture with a diluent, e.g. saline, or a unit dose of one of the compounds admixed with a carrier in the form of a tablet, capsule or ampule. The compositions can be used for treating a disorder in learning or memory; or alcohol or benzodiazepine dependence by administering to a patient in need thereof an amount effective therefore of one of the above compounds.

Other features and advantages of the invention will be apparent from the following description of the preferred embodiments thereof, and from the claims.

DESCRIPTION OF THE PREFERRED EMBODIMENTS

The drawing is first briefly described.

Drawing

The FIGURE is a group of structural representations of various known compounds having affinity for BZD receptors, as discussed above.

Structure

The compounds of the invention have the general formula recited in the Summary of the Invention above Examples of preferred compounds within this formula are those referred to as preferred embodiments above. The compounds can also be provided in the form of pharmaceutically acceptable salts. Examples of suitable salts include those formed with hydrochloric, hydrobromic, sulfuric, maleic, acetic, or fumaric acid.

Synthesis

The compounds of the invention ca be synthesized generally as described by Boltze et al., supra. Below are examples of such syntheses. Those in the art will recognize that other examples of the claimed compounds can be synthesized according to the general methods of these examples.

Generally, a 3-aminobenzodiapine of formula 2

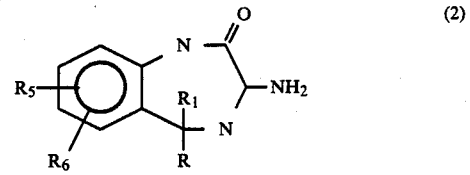

(where each group is as defined above) is condensed with a compound of formula 3

(where each group is defined as above, and $R_{14}$ can be hydrogen methyl or ethyl). A compound of formula 2 can be prepared from a 3-hydroxy compound using published methods (4 J. Het. Chem. 647, 1967; 29 J Org. Chem 1695, 1962; and U.S. Pat. No. 3,198,789) or from a 1,3-dihydrobenzodiazepine-2-one (e g., E.P. 167.919). A compound of formula 3 can be prepared from commercially available meldrum acid and trimethyl or triethylorthoformate, and some are commercially available (e.g dimedone, 5,5 dimethyl 1,3-cyclohexanedione) Resolution of the resulting 3-aminobenzodiazepines ca be achieved by published methods e.g., as described in 52 J. Org. Chem 955, 1987. The condensation reactions are preferably carried out in an inert organic solvent, e.g., an alcohol, ethoxyethanol, diemthoxyethane, tetrahydrofuran, dimethylformide, dichloromethanol, or chloroform with the reaction temperature maintained at between 22° C. and 100° C., most preferably, room temperature. The intermediates and final products are isolated and purified by standard methods, e.g., column chromatography or crystallization. Purity is determined using chromatographic, spectroscopic, and chemical analysis

EXAMPLE 1

1,3-dihydro-1-methyl-3-oximino-5-phenyl-2H-1,4-benzodiazepine-2-one 20 ml of tert-butylalcohol were added to a suspension of potassium tert-butoxide (2 to 5 g) in 60 ml dry tetrahydrofuran at −20° C. under nitrogen. A solution of 1,3-dihydro-1-methyl 5-phenyl-2H-1,4-benzodiazepin-2-one (2.5 g) in 25 ml of tetrahydrofuran was then added dropwise. The resulting dark amber colored solution was stirred for 2 hours at −20° C. and treated with 1.74 ml of isoamylnitrite. The dark red solution was then warmed to 0° C. over 15 minutes and quenched with a solution of 6 ml ice-cold water and 2 ml acedic acid The solvents were removed in vacuo and the residue partitioned between ethylacetate and brine. Organic extracts were dried using $Na_2SO_4$, and then concentrated. The resulting semi-solid compound was triturated with ether to give 2 23 g of a yellow-tan colored product, having an $R_4=0.12$ in silica gel chloroform/acetone $=9:1$ (TLC).

EXAMPLE 2

3(RS)-amino 1,3-dihydro-1 methyl 5-phenyl-2H-1,4-benzodlazepin-2one

A solution of 2.0g of 1,3-dihydro-1-methyl-3-oximino-5-phenyl-2H-1,4 benzodiazepin 2-one in 60 ml of ethanol was treated with a slurry of Raney nickel (4 g) in 20 ml of ethanol The resulting suspension was hydrogenated under 60 p.s.i. at 20–25° C. The catalyst was filtered off with a celite pad and the filtrate concentrated to provide 2.0 g of product having an $R_f=0.49$ on TLC.

EXAMPLE 3

2,2-dimethyl 4,6-dioxo-5-methoxymethylene-1.3-dioxane 10g of meldrum acid were dissolved in 39 ml of trimethylorthoformate and the mixture refluxed at 90° C. under nitrogen atmosphere for 3 hours. After cooling at room temperature, pale yellow solid was collected by filtration. washed with a small amount of trimethylorthoformate, petroleum ether, then dried to yield 7.8 g product.

EXAMPLE 4

3-(RS)-1,3-dihydro-3-(2,3-dimethyl-4,6-dioxo-1,3-dioxane-5-ylidenemethyl)amino-1-methyl 5 phenyl-2H-1,4-benzodiazepan-2-one A solution of 3-(RS) amino-1,3 dihydro-1-methyl-5-phenyl-2H 1,4 benzodiazepin 2-one (0.33g with slight impurities), and 2,2-dimethyl-4,6-dioxo-5-methoxymethylene-1, 3-dioxane (0.186 g) in 10 ml of ethanol was refluxed for 3 hours and cooled to 20–25° C. The resulting colorless solid was collected by filtration, washed with cold water, and dried to yield 0.28 g product having an $R_f=0.27$ in TLC.

The compounds of the invention can be made into pharmaceutical formulations which include non-toxic. inert, pharmaceutically suitable excipients The formulations may be provided in the form of individual tablets, capsules, pills, suppositories and ampules, in which the content of active compound corresponds, e.g., to a fraction of an individual dose for a human patient. Such tablets can contain the active compound or compounds alongside the customary excipients, such as fillers, binders, humectants, disintegrating agents, solution retarders, absorption accelerators, wetting agents, adsorbents, and lubricants. The active compound or compounds, optionally together with one or more of the above-mentioned excipients, can also be in microencapsulated form.

The active compounds or the pharmaceutical formulations can be administered orally, parenterally rectally, or intravenously. In general, it is advantageous to administer the active compound or compounds in amounts of about 0 01 to about 10, preferably 0.1 to 1 mg/kg of body weight every 24 hours in the case of parenteral (intravenous or intramuscular) administration, and in amounts of about 0.05 to about 100, preferably 0.1 to 10 mg/kg of body weight every 24 hours in the case of oral administration, if appropriate in the form of several individual doses, in order to achieve the desired results. An individual dose preferably contains the active compound or compounds in amounts of about 0.01 to about 30, in particular 0.05 to 3 mg/kg of body weight.

Other embodiments are within the following claims We claim:

1. A benzodiazepine of the formula:

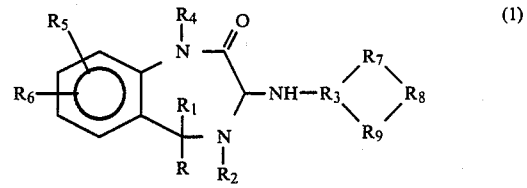

(1)

where:
R represents H, alkyl, alkenyl, cycloalkyl or cycloalkenyl, each with up to 8 carbon atoms; phenylalkyl with an alkylene chain of 1 to 3 carbon atoms and optionally substituted on the phenyl radical with one or two substituents each selected from the group consisting of Cl, Br, F, CN, $CF_3$, $NO_2$, lower alkyl, and $OCH_3$; or represents a phenyl radical which is optionally substituted with one or two substituents selected from the group consisting of Cl, F, Br, CN, I, $CF_3$ $NO_2$, lower alkyl, and $OCH_3$, or represents a 5-membered or 6-membered heterocyclic radical with 1 or 2 heteroatoms from the group consisting of O, N and S;
$R_1$ represents H or, together with $R_2$, forms a bond;
$R_2$ and $R_4$ independently of one another represent H or an alkyl radical with 1 to 6 carbon atoms, or represent a phenylalkyl radical with an alkyl chain of 1 to 3 carbon atoms and optionally substituted on the phenyl radical with one or two substituents each selected from the group consisting of Cl, Br, F, CN, $CF_3$, $NO_2$, lower alkyl, and $OCH_3$;
$R_2$ together with $R_1$, forms a bond;
$R_5$ and $R_6$ independently of one another represent H, Cl, Br, F, CN, $CF_3$, $NO_2$, lower alkyl, or $OCH_3$;
$R_3$ is $(CH_2)_n CH$ where n is between 0 and 5 inclusive; or $(CH_2)_n CR_{14}=CR_{14}$; wherein $R_{14}=H$ or about
$R_7$ and $R_9$ are independently $CH_2$ or $C=O$;
$R_8$ is

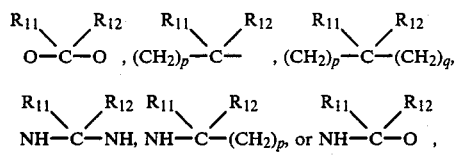

p and q are independently between 0 and 4 and the sum of p and q is 4 or less;
m is between 2 and 4 inclusive; and
$R_{11}$ and $R_{12}$ are independently 4 or a lower alkyl of between 1 and 5 carbon atoms.

2. The benzodiazepine of claim 1, wherein R is

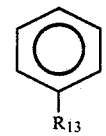

$R_{13}$ is H or a halogen;

$R_1$ is H;
$R_2$ is H;
$R_4$ is H or lower alkyl; and
$R_5$ and $R_6$ are independently H or a halogen.

3. The benzodiazepine of claim 1 or claim 2 wherein $R_3$ is CH=CK.

4. The benzodiazepine of claim 3 wherein at least one of $R_7$ or $R_9$ is C=O.

5. The benzodiazepine of claim 4 wherein $R_8$ is

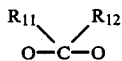

6. The benzodiazepine of claim 5 wherein $R_{11}$ and $R_{12}$ are both H.

7. A benzodiazepine selected from the group consisting of 3(RS) 1,3-dihydro-3(2,2-dimethyl-4,6-dioxo-1,3-dioxan-5-ylidenemethyl)amino-1-methyl-5-phenyl-H,1,4-benzodizepin-2-one; 3(RS)-1,3-dihydro-3-(2,2dimethyl-4,6-dioxo-1,3-dioxan-5-ylidenemethyl)amino-7-chloro-1-methyl-5-phenyl-2H,1,4-benzodiazepin-2-one; and 3(RS)-1,3-dihydro-3-(2,2-dimethyl-4,6-dioxo-1,3-dioxan-5-ylidenemethyl)amino-7-fluoro-1-methyl-5-phenyl 2H, 1,4-benzodiazepin-2-one.

8. A composition for treating cerebral disorders comprising an amount effective therefore of a compound according to claim 1 in admixture with a diluent or carrier.

9. A unit dose of a composition according to claim 8 in the form of a tablet, capsule or ampule.

10. A method for treating a disorder in learning or memory which comprises administering to a patient in need thereof an amount effective therefore of the compound of claim 1.

11. A method for treating a disorder in learning or memory which comprises administering to a patient in need thereof an amount effective therefore of the composition of claim 8.

12. A method for treating alcohol or benzodiazepine dependance which comprises administering to a patient in need thereof an amount effective therefore of the compound of claim 1.

13. A method for treating alcohol or benzodiazepine dependance which comprises administering to a patient in need thereof an amount effective therefore of the composition of claim 8.

* * * * *

UNITED STATES PATENT AND TRADEMARK OFFICE
CERTIFICATE OF CORRECTION

PATENT NO. : 4,957,915

DATED : September 18, 1990

INVENTOR(S) : Sun H. Kim et al

It is certified that error appears in the above-identified patent and that said Letters Patent is hereby corrected as shown below:

On the title page, item [56] under "FOREIGN PATENT DOCUMENTS", insert --SWISS PATENT NO. 494,765, AUG/13/70--;

COL. 2, LINE 39, CHANGE "$R_{14}=H_{06}$ OR" TO ---$R_{14}$=H OR A BOND--;

COL. 5, LINE 3, CHANGE "$R_4$" TO --$R_f$--;

COL. 6, CLAIM 1, LINES 26-28, AFTER "$OCH_3$", DELETE "OR REPRESENTS REPRESENTS A 5-MEMBERED OR 6-MEMBERED HETEROCYCLIC RADICAL WITH 1 OR 2 HETEROATOMS FROM THE GROUP CONSISTING OF O, N AND S";

COL. 6, CLAIM 1, LINE 42, DELETE "OR ABOUT" AND INSERT INSTEAD --OR A BOND--;

COL. 6, CLAIM 2, AT THE BOTTOM OF THE PAGE BEFORE "$R_{13}$", INSERT --WHERE--;

COL. 7, CLAIM 3, LINE 6, CHANGE "CH=CK" TO --CH=C--;

UNITED STATES PATENT AND TRADEMARK OFFICE
CERTIFICATE OF CORRECTION

PATENT NO. : 4,957,915
DATED : September 18, 1990
INVENTOR(S) : Sun H. Kim et al It is certified that error appears in the above-identified patent and that said Letters Patent is hereby corrected as shown below:

COL. 7, CLAIM 7, LINE 21, "H,1,4-BENZODIZEPIN-" SHOULD BE --2H,1,4-BENZODIAZEPINE--;

Signed and Sealed this

Ninth Day of June, 1992

Attest:

DOUGLAS B. COMER

Attesting Officer       Acting Commissioner of Patents and Trademarks

UNITED STATES PATENT AND TRADEMARK OFFICE
CERTIFICATE OF CORRECTION

PATENT NO. : 4,957,915

DATED : Sept. 18, 1990

INVENTOR(S) : Sun H. Kim and John E. Taylor

It is certified that error appears in the above-identified patent and that said Letters Patent is hereby corrected as shown below:

Column 5, line 2, "2 23 g of" should be --2.23 g of--.

Column 5, line 61 "about 0 01 to" should be --about 0.01 to--.

Signed and Sealed this

Sixth Day of October, 1992

Attest:

DOUGLAS B. COMER

Attesting Officer

Acting Commissioner of Patents and Trademarks